(12) United States Patent
Friedman

(10) Patent No.: US 6,423,697 B1
(45) Date of Patent: Jul. 23, 2002

(54) INTRAORAL TOPICAL ANTI-INFLAMMATORY TREATMENT FOR RELIEF OF MIGRAINE, TENSION-TYPE HEADACHE, POST-TRAUMATIC HEADACHE, FACIAL PAIN, AND CERVICAL-MUSCLE SPASM

(76) Inventor: Mark Friedman, 5 Forest Ct., Larchmont, NY (US) 10538

( * ) Notice: Subject to any disclaimer, the term of this patent is extended or adjusted under 35 U.S.C. 154(b) by 0 days.

(21) Appl. No.: 09/626,250

(22) Filed: Jul. 26, 2000

Related U.S. Application Data

(60) Provisional application No. 60/115,940, filed on Jan. 14, 1999.

(51) Int. Cl.⁷ .......... A01N 37/36; A01N 43/26; A01N 37/10; A61K 31/19; A61K 31/335
(52) U.S. Cl. .......... 514/164; 514/165; 514/463; 514/568; 514/570
(58) Field of Search .......... 424/434; 514/164, 514/165, 463, 568, 570

(56) References Cited

U.S. PATENT DOCUMENTS 5,407,663 A * 4/1995 Eisen .......... 424/49
6,139,861 A * 10/2000 Friedman .......... 424/435

FOREIGN PATENT DOCUMENTS

DE      19715594      * 10/1998

* cited by examiner

Primary Examiner—Alton Pryor
(74) Attorney, Agent, or Firm—Evelyn M. Sommer

(57) ABSTRACT

An anti-inflammatory, either a NSAID or glucocorticoid steroid in the form of an ointment, cream, lotion, gel, powder, tablet, paste, film, tape or adhesive bandage, provided with appropriate vehicle to allow specific adherence to specific gingival areas, for topical treatment of inflammation. This composition and the method of using same is used to prevent or relieve migraine, tension-type headache, post-traumatic headache, facial pain and cervical muscle spasm.

4 Claims, 4 Drawing Sheets

Intra-oral Site of Tenderness (arrows)

Maxillary Nerve Plexus (arrows)

INTRAORAL TOPICAL ANTI-INFLAMMATORY TREATMENT FOR RELIEF OF MIGRAINE, TENSION-TYPE HEADACHE, POST-TRAUMATIC HEADACHE, FACIAL PAIN, AND CERVICAL-MUSCLE SPASM

This application claims the priority of Provisional Application Ser. No. 60/115,940 filed Jan. 14, 1999.

This invention relates to a method for treatment of migraine, tension-type headache, post-traumatic headache, facial pain and cervical-muscle spasm. More particularly the invention relates to a method of treatment which is non-invasive, non-toxic and non-sedating. The method of the invention comprises delivering a composition, topically, to a specific intraoral area of tenderness consistently noted in patients with headache that appears closely associated with several painful conditions: migraine, tension-type headache, post-traumatic headache, facial pain and cervical-muscle spasm. The composition comprises at least one member of the group of anti-inflammatory agents, NSAIDS or glucocorticoid steroids dissolved, distributed or dispersed in a suitable carrier for topical administration to the intraoral area of tenderness which has been found to be associated with the afore-noted conditions.

BACKGROUND OF THE INVENTION

A distinct area of maxillary alveolar tenderness is consistently noted in patients with headache: vascular, tension-type, post-traumatic, even in the headache-free state (asymptomatic patients) (1). This area has consistently been identified in patients suffering from facial pain (2) or posterior cervical muscle hyperactivity (spasm) (3). This zone of tenderness, usually absent or minimal in the normal state (2), occurs in the maxillary third molar apical area (FIG. 1) even if edentulous, and correlates closely with a plexus formed by the posterior superior alveolar branch of the maxillary nerve (FIG. 2, arrows).

In preliminary data analysis, 1026/1100 (93.2%) mostly asymptomatic migraine patients exhibited maxillary alveolar tenderness, with laterality and degree of tenderness closely related to laterality and severity of symptoms. This consistent finding has been corroborated by several neurologists.

In a pilot study of thirty asymptomatic migraine patients with a unilateral history, blinded, inexperienced examiners selected the symptomatic side in 27/30 (90%) patients, based on the laterality of intraoral palpation findings.

The following evidence associates this tender area with a localized inflammation:

In 18 consecutive patients with atypical facial pain (recently reclassified as facial pain, (International Headache Society) (4), ipsilateral tenderness and increased temperature were found in 15 and 17 patients, respectively; in two control groups, often patients, no significant association was observed between the area associated with maxillary tenderness and increased temperature (1). A YSI (Yellow Springs International) Model 43TA tele-thermometer covered by a disposable plastic sheath was used bilaterally to record temperatures (2).

A similar experiment (intraoral palpation, temperature recording) was performed on 40 patients during unilateral episodic migraine or tension-type headache in the departments of Neurology, Dentistry, Emergency Medicine (Westchester Medical Center, Valhalla, N.Y.) a private practice limited to oromandibular dysfunction (MHF, Mt. Vernon, N.Y.), and Our Lady of Mercy Hospital (Bronx, N.Y.). The posterior maxillary molar periapical areas were palpated bilaterally for tenderness, and their temperatures were recorded, as in the previously described facial pain experiment (2). Significant correlations were found between severity and laterality of symptoms to tenderness, and between temperature and tenderness differentials. Kappa statistics demonstrated good agreement between laterality of temperature differential and tenderness, and laterality of highest temperature and symptoms (1).

An intraoral vasoconstriction device was used on 12 patients with cervical pain and muscle spasm. Ice water circulating through hollow metal tubes shaped to fit the maxillary area of tenderness was held intraorally for 15 minutes on this area of tenderness, on these 12 patients. In 9 of these individuals, reduced cervical pain perception, upper trapezius electromyography signal reduction, and increased range of motion was produced. Six out of 12 individuals had accompanying headache, which was reduced or eliminated in 4 cases (3). This device, as used in the maxillary area of tenderness, has been cleared by the U.S. Food and Drug Administration for muscle spasm reduction (K955529).

In the emergency departments at Westchester Medical Center and Sound Shore Medical Center, 25 acute migraine and tension-type, headache patients were similarly treated by intraoral chilling, for 40 minutes. Treatment was supervised by eight non-blinded emergency medicine physicians. Patient ratings of pain (all patients) and nausea (migraine patients only), on a scale from 1 to 10, (10=most severe) pre- and post-treatment and 24 hours post-treatment ratings were recorded. Initial baseline and immediate post-treatment headache intensities were 7.7 and 3.0 respectively. Baseline and post-traumatic nausea intensities (19 migraine patients only) were 5.9 and 1.6 respectively. The mean reduction in headache score was 4.7 ($p<0.0005$), and that for nausea was 4.3 ($p<0.005$). No side-effects were reported or observed. Of the 25 patients, the 19 who were able to be followed for up to 24 hours showed a further significant decrease in pain, but not in nausea. No medications were given to the 20 patients whose headaches were relieved or eliminated by the 40 minute treatment. This local vasoconstrictive effect is in contrast to the systemic vasoconstriction produced by the specific anti-migraine medications.

Results of this study also demonstrated the effectiveness of application of intraoral circulating ice water applied to the posterior maxillary area for resolving symptoms related to head and neck pain (cervical pain and muscle spasm) secondary to neurogenic inflammation. Nine of 12 patients with cervical pain and muscle spasm treated for 15 minutes showed reduced cervical pain perception, upper trapezius electromyography signal reduction, and increased cervical range of motion. Findings from this study suggest a strong trigemino-cervical relationship to head and neck pain and headache.

Other studies have also suggested that a strong connection exists between trigeminal and cervical motor and sensory responses.

These experiments suggest that the intraoral marker, (area of maxillary alveolar tenderness), for the above pain disorders, is a local inflammation, associated with increased local blood flow (vasodilation) and edema. The increased local temperature and tenderness are classic signs of inflammation, and the significant response to local cooling is caused by edema (swelling, another classical sign of inflammation) resolution.

The treatment location is also significant. The maxillary alveolar tenderness is located in an area that permits access to the trigeminal system where it is unprotected by skin or bone. In a recent experiment, somatosensory trigeminal evoked potentials (STEP) were done on 12 healthy volunteers with no history of head or neck pain. The electrical input point was over the left infraorbital foramen. After a base-line STEP, low power helium-neon laser (1.7 mW, 632.5 nm, 50 Hz) was applied by light tissue contact, to the left apical third molar area for two minutes. This resulted in an immediate average STEP amplitude reduction of 61%, with further reduction of 65.2 and 71.8%, ten and 20 minutes later. These results, far in excess of any analgesic intervention studies, demonstrate significantly greater amplitude reduction than that produced by 150 mg Demerol.

The object of this invention is to reduce or eliminate this intraoral inflammation localized in the maxillary third molar apical area, and associated with the medical conditions listed above, by local anti-inflammatory treatment. Oral anti-inflammatory medications aspirin, Excedrin, Ibuprofen, Tylenol, Naproxen etc. have been proven to be mildly effective for headache (5, 6, 7). However, even with limited effectiveness, significant blood levels are produced by these medications, often precluding long-term use. A large scale topical NSAID study (23,590 patients) showed only 6 cases of possible adverse GI events (8).

Figure 4:
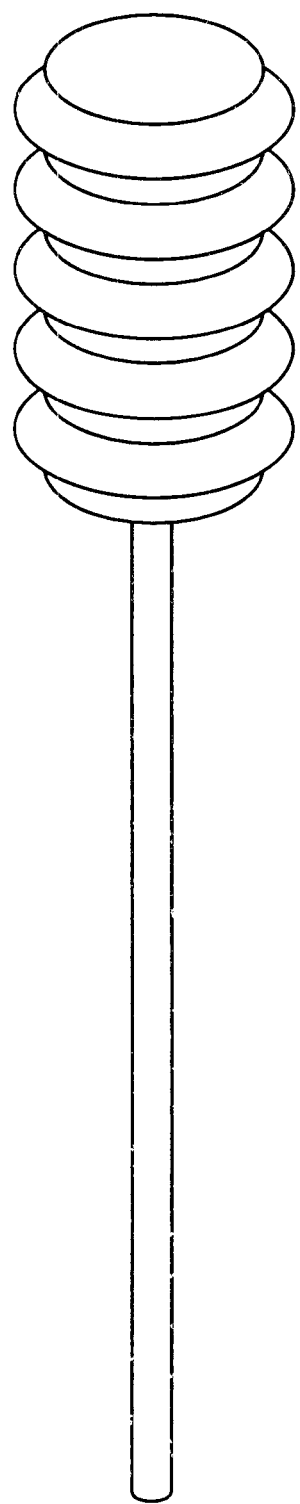
FIG. 4 Bulb insufflator for dispensing powder.
Figure 5:
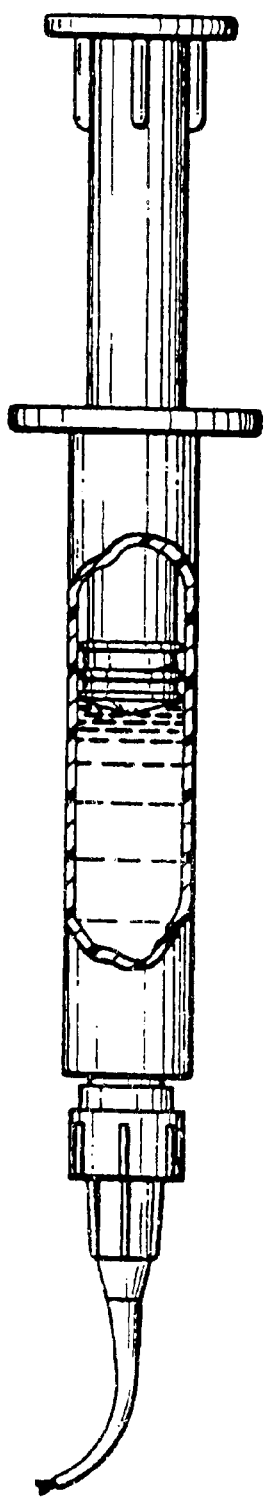
FIG. 5 Illustrates a preferred device for administering medication to the prescribed area.

In accordance with the invention, the topical application of a combination of at least one member of anti-inflammatory medication(s) (NSAID and or a glucocorticoid steroid), dissolved, dispersed or distributed in a suitable carrier useful in delivering and enabling adherence of the medication to the mucous membrane of the mouth is formulated. The invention also embodies specific placement of this composition (anti-inflammatory agent and carrier) to the periapical areas of the posterior molar teeth (the area of maxillary alveolar tenderness), in cases of migraine, tension-type headache, post-traumatic headache, facial pain and cervical muscle tenderness. The compositions can be applied in the form of ointments, creams, lotions, gels, powders or pastes with or without occlusion by films or tapes or via specific adhesive bandages. The method of dispensing the composition is determined by the carrier used for its preparation. Appropriate application could be made by dispensing to the specific area via the finger tip, cotton swab, a plastic dental syringe, an intraoral adhesive bandage or by a spray insufflator, such as the one shown in FIG. 4 or by a No. 119 DeVilbiss spray atomizer. Controlled rate absorption can be accomplished with certain delivery systems available commercially.

Absorption from oral mucosa has special significance drugs, despite the fact that the surface area is small. Venous drainage from the mouth is to the superior vena cava; significantly the drug is protected from rapid first pass metabolism by the liver. The rate of absorption through the mucous membrane is rapid. Another advantage of absorption from the oral mucosal membrane is the elimination of the effect of food intake on the rate and on the resulting concentration of the pharmacological agent during the absorption process. The exposure of the active agent to the low pHs of the stomach is also avoided.

The invention also contemplates adjusting the saturation concentration of a drug in a transdermal composition for application to the mucous membrane of the mouth. This can be accomplished, for example, by mixing polymers having different solubility parameters, so as to modulate delivery of the drug. This results in the ability to achieve a predetermined permeation rate of the drug into and through the mucous membrane. In one embodiment, a composition of the present invention comprises a drug, an acrylate polymer, and a polysiloxane. The compositions can be produced by a variety of methods known in the preparation of drug containing adhesive preparations, including the mixing of the polymers, drug and additional ingredients in solution followed by removal of the processing solvents.

The method and composition of the invention permits selective loading of the drug into the formulation and adjustment of the delivery rate of the drug from the composition through the mucous membrane while maintaining acceptable shear, tack and peel adhesive properties.

The following vehicles, carriers, preparations and delivery systems for dispensing the anti-inflammatory compositions are particularly suitable for maintaining a medication at the site of application on the mucous membrane.

A matrix technology is available from Noven Pharmaceuticals Inc. which utilizes a matrix technology in which the adhesive functions as both the drug platform and as a means of affixing the system to the patient. The patch delivers a drug, for example, steroid, through the mucous membrane and into the blood stream continuously for up to three days.

Several other transmucosal therapeutic systems have been developed to study enhanced/controlled delivery of drugs through the oral mucosa over a prolonged period of time. These systems are usually bilayers consisting of fast-release and sustained release layers.

3M is a company involved in transmucosal drug delivery systems including patch designs.

A patch design has been proposed by another company consisting of four layers of thin flexible membranes, an impermeable backing, a drug reservoir, a rate controlling membrane plus an adhesive. When the patch is applied, the drug begins flowing through the mucous membrane into the blood stream at a rate regulated by the membrane, preprogrammed to keep the drug at levels that provide effectiveness without adverse effects.

Another type of mucoadhesive patch for transmucosal delivery of pharmacological agents is one prepared from Carbopol 974P and silicone polymer.

Patches are easy to apply and remove, non-irritating to tissue, and able to continuously deliver a drug over an extended period of time.

A bandage is available for use in continuous administration of drugs to the oral mucosa, comprising a backing member defining one exterior surface, a surface of pressure-sensitive adhesive defining a second exterior surface, and disposed there between a reservoir containing drug formulation. The reservoir can comprise a distinct layer of the bandage or a plurality of microcapsules distributed throughout the adhesive surface.

Another means for mucosal administration of a drug is comprised of a support member, which is water insoluble, waterproof and flexible, a moisture activated, adhesive precursor applied to one surface of the support member and an active ingredient applied to the central portion of the support member either directly or dispersed in a matrix. When applied to the oral mucosa, contact with saliva activates the adhesive and causes the support member to adhere to the desired area, thereby exposing the active ingredient to a limited area of the oral mucosa while isolating the active ingredient from the remainder of the oral environment. The moisture-activated adhesive precursor is comprised of a hydrocolloid admixed with polyvinylpyrrolidone applied to the support member.

Mucoadhesive erodible tablets can also be used and are prepared using different bioadhesive polymers along with excipients like mannitol and PEG-6000. Examples of such polymers are carbopol-934 and sodium-carboxymethylcellulose.

Another composition for an erodible mucoadhesive tablet is formulated with polyacrylic acid, and hydroxymethylcellulose. The adhesive quality is determined by the concentration of the polyacrylic acid; the greater the concentration of the polyacrylic acid the greater the adhesive force. Pharmacological agents are added to the bioadhesive tablet by directly compressing with the polymers.

Orabase® is a patented product sold without prescription. One such product is ORABASE® Plain marketed by the Colgate Co. Chemically Orabase consists of plasticized hydrocarbongel, guar gum, carboxymethylcellulose, tragacanth gum and pectin. Orabase is an adhesive-vehicle protectant preparation and was designed especially for the purpose of retaining topically applied drugs on the oral mucous membranes. Studies with this preparation have indicated that it adheres to the oral mucosa for 2 hours or longer, the duration being dependent on the degree of mobility of the oral tissues, the washing action of saliva and the amount of vehicle applied. Owing to its physical properties, which favor prolonged adherence, Orabase offers the following potential advantages over previously used vehicles: (1) increased contact-duration time of the tissues with the active component, (2) increased effectiveness of the active component by maintenance of a higher concentration at the desired site, (3) decreased amount of an active material which needs to be applied at any one time, (4) decreased total dosage of active medication—highly desirable in many instances from a systemic-activity point of view, and (5) marked protective action.

Approximately 100 to 250 mg of the adhesive vehicle, with or without a therapeutic agent is applied to the desired site, in the form of thin film. Orabase is without any toxic or irritant properties and is most often applied to oral, open lesions without consequence.

Other formulations are available for oral adhesive pastes. One such oral adhesive paste consists of equal parts of gelatin, pectin, and sodium carboxymethylcellulose in a base of plasticized 50W in xanthum gum.

Adhesive vehicle formulations, using almost any powder denture adhesive as the vehicle, have been prepared. Formulations of this type containing medication may be applied by a spray insufflator (spray atomizer No. 119 DeVilbis) or by the spray instrument pictured in FIG. 4. Adhesion of the powder vehicle to the oral mucosa has been found to be very satisfactory, and it has proved to be more effective than the paste for reaching less accessible oral lesions, since by properly manipulating the spray dispenser nearly every specific site of the oral cavity can be reached. The powder vehicle has proved to advantageous in still another respect; i.e., it can be applied evenly to as large an area as is indicated. Furthermore, the thinness of the film which is applied is easily controlled. Almost any drug available as a powder, tablet, caplet etc., can be mixed with almost any adhesive denture powder or gel and the resulting applied by previously described methods.

The therapeutic results obtained through the use of active drugs incorporated in the adhesive powder vehicle (Orahesive) parallel closely the results obtained from the use of the same drugs in equal concentrations prepared in the paste (Orabase).

Adherent powders are made from finely powdered gums such as karaya, acacia or tragacanth. The powders are prepared by mixing several of the gums or by the use of one alone. They may be flavored. These materials swell to many times the original volume on the addition of water (or saliva) and assume mucinalagenous or gelatinous properties.

An intraoral adhesive bandage is used as a protectant and can be used as a carrier of medication or to serve as a protectant for topically applied medication or as an occlusive dressing.

There are numerous gels and pastes commercially available e.g. Duralast Gel® (Schering-Plough).

There are film forming materials suitable for application to the oral mucosa; one such example is Zilactin® (Zila Pharmaceuticals Inc.). Zilactin is a hydroxypropyl cellulose film former. In use it forms a tenacious, occlusive film which holds the medication in place. Intraorally the film can last up to 8 hours (average duration of mucosal adherence was 3.92 hours). The gel dries 30–60 seconds after application.

Many preparations of adhesive compounds useful for treatment of mucosal pain and infection are available as nonprescription drugs and are used widely; they contain analgesic materials as well as antibiotics.

Under certain conditions, compositions containing NSAID and/or steroid could be prepared in lotions, creams or ointments. The active agent is added to the cream or ointment base as a micronized powder or in some instances as a solution.

The adhesive materials or Orahesive bandage can be prepared for use either by impregnating the active agent in a drug reservoir or by using the material as an occlusive dressing or as a protectant, the active agent being applied to the adherent surface. The drug containing materials may then be placed directly on the area of tenderness.

Several different types of rate controlling drug delivery systems are available and have application for use on mucous membranes. Two types are briefly described: (1) Consists of 5 layers and is assembled as follows: a transparent polyester film, a drug reservoir-gelled with hydroxpropyl cellulose, an ethylene-vinyl acetate copolymer membrane, an adhesive formulation of light mineral oil and polyisobutylene and a protective layer of siliconized polyethylene terphthalate film; the latter layer being removed before use. (2) Consists of 3 layers and is assembled as follows: an outer backing layer composed of a laminated polyester film, a middle layer containing a rate controlling adhesive a structural nonwoven material and a disposable layer that is removed before use. All the components making up the rate controlling delivery system are inactive. Some of these delivery systems are available as small sheets and can be cut into sizes appropriate for use.

In another embodiment of the present invention, iontophoresis can be used to deliver an appropriate medication beneath the mucous membrane to the inflamed area. The use of direct current (galvanism) in iontophoresis is based on the fact that when a current passes through a salt solution there is ionization of the salt, the positive ion being repelled by the anode (the positive electrode) and the negative ion being repelled by the cathode (the negative electrode). Various substances that dissociate or form ions in solution have been identified as useful in treating soft tissue conditions such as inflammation. Readily available among these substances are the salicylates, hydrocortisone, and dexamethasone. They can be applied to the area in cream form, or in solution applied to a gauze; in both instances, the current will drive the medication subdermally.

Non-steroid Anti-inflammatory Drugs (NSAIDS) to be Used in Compositions Alone or in Combination with a Glucocorticoid Steroid Aspirin—salicylic acetate $C_9H_8O_4$ MW 180.16—used as a antipyretic, analgetic, and anti-inflammatory. Indicated for relief of pain from headache, discomfort of fever, and minor muscular aches and pains. Following oral administration peak plasma levels are reached within 1–2 hours and maintained for 4–6 hours. Plasma half-life ranges from 4.7–9 hours.

Ibuprofen—2-(p-Isobutyl phenyl) propionic acid $C_3H_{18}O_2$ MW 206.27—a non steroidal anti-inflammatory agent that possesses analgesic, anti-inflammatory and anti-pyretic activities. The drug is rapidly absorbed after oral administration and peak plasma levels are attained within 1–2 hours; the half-life is 1.8–2.0 hours.

Naproxen—6-methoxy methyl-2-naphtalene acetic acid $C_{14}H_{14}O_6$ MW 230.26—a non-steroidal compound that has anti-inflammatory, analgesic and antipyretic activity. Peak plasma levels are reached in 24 hours. The mean plasma half-life is about 13 hours.

Ketoprofen—2-(3benzoxyphenyl)-propionic acid $C_{16}H_{14}O_3$ MW 254.29—a non-steroidal compound that has anti-inflammatory, analgesic, and antipyretic activity. Peak plasma levels are reached in 0.5–2 hours; the half-life is 2–4 hours.

The NSAIDS have been shown to have inhibitory effects on prostaglandin and leukotriene synthesis, to have anti-bradykinin activity as well as to have lysosomal stabilizing action.

Glucocorticoid Steroids to be Used in Compositions with or without NSAIDS

A listing of such agents, useful in this invention, and their relative pharmacologic activity in approximately equivalent doses is as follows:

| | |
|---|---|
| cortisone* | 25 mg |
| hydrocortisone* | 20 mg |
| prednisone | 5–10 mg |
| prednisolone | 5 mg |
| triamcinolone** | 0.7 mg |
| clobetasol propionate*** | 0.5 mg |
| fluocinonide*** | 0.5 mg |
| fluocinolone*** | 0.1 mg |

*only 2 naturally occurring glucocorticoid steroids
**Triamcinolone acetonide one of the more efficacious corticosteroids prepared in a adhesive vehicle, it is marketed as (Kenalog - Bristol Meyers) in an adhesive vehicle (Orabase). ORABASE HCA (hydrocortisone 0.5% in orabase) is also available
***high potency topical steroids The above steroids exhibit different solubilities and thus rates of absorption. They are prepared as solutions, suspensions, creams, gels, ointments and tablets. Application and preparation of medicaments for use is determined by the physical and chemical properties of the composition.

Orabase as the dispensing carrier requires no special apparatus for applications and allows for accurate and controlled application of medicament to the site of inflammation; 0.06 to 0.25 ml is the volume regularly used. Kenalog (triamcinolone in orabase Bristol Meyers) is available commercially. This can be used alone or with an NSAID, e.g., aspirin or ibuprofen could be introduced into the Kenalog taking advantage of the additive, or possibly synergistic differing pharmacological properties of each medicament. (Both NSAIDS and glucocorticoid steroids are anti-inflammatory but act to reduce inflammation by different mechanisms). The NSAIDS could be incorporated into the adhesive powder vehicle or prepared in the paste and applied by dental syringe, spray atomizer or cotton tipped applicator.

If application of composition, for periods greater than two hours are desired the Orahesive bandage could be superimposed at the time of initial application of medicament. The bandage is protective as well as occlusive and thereby increasing absorption.

Steroids dispensed in liquid, lotion, cream or ointment could be used with the adhesive bandage directly or added to the paste.

Any of the vehicles (modified adhesive bandage) for controlled release of medicament could be used for drug delivery.

Figure 1:
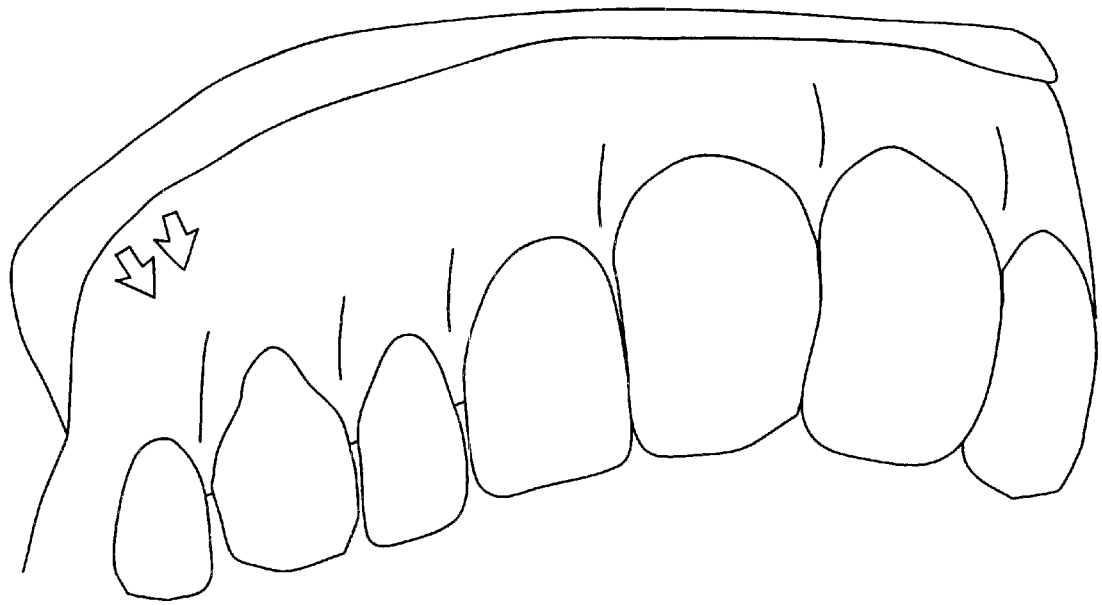
FIG. 1 Zone of tenderness located in the periapical (root tip) area of the maxillary third molar, even if the tooth is missing.
Figure 2:
FIG. 2 Zone of tenderness (arrows), located in the plexus formed by D; A facial nerve; B sphenopalatine ganglion; C infraorbital nerve; D the posterior superior alveolar branch of the maxillary nerve.
Figure 3:
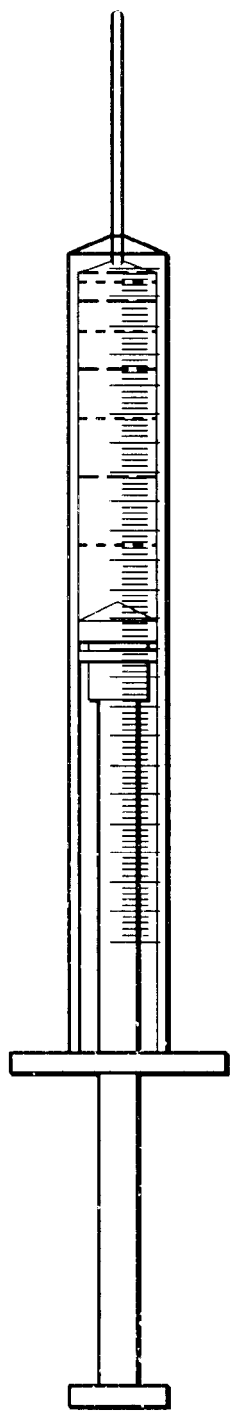
FIG. 3 Plastic dental syringe filled with medication.

In accordance with a preferred embodiment of the invention Ketoprofen is incorporated by thorough admixing the same in an amount of 10%–20% into an oral adhesive paste, consisting of equal parts of gelatin, pectin and sodium carboxymethylcellulose in a base of plasticized 50 W in xanthum gum. The resulting mixture is applied to the patient needing treatment with the small plastic syringe shown in FIG. 3.

The following examples will serve to illustrate the invention:

EXAMPLE 1

A paste formulation containing the non-steroid anti-inflammatory agent Ketoprofen is prepared by thoroughly mixing Ketoprofen in a final concentration of 20% (w/w) into an oral adhesive paste. The paste is compounded of equal parts of gelatin, pectin and sodium carboxymethylcellulose. in a base of plasticized 50 W in Xanthum gum. The resulting mixture passes easily through a 1 ml syringe. Topical application of the mixture is made directly to the area of maxillary alveolar tenderness in 60 mg (0.06 ml) to 250 mg (0.25ml) amounts using a small syringe.

EXAMPLE 2

A formulation comprising the glucocorticoid triancinolone acetonide pre-prepared in and adhesive vehicle, orabase (Kenalog®) to which is added with thorough mixing a non-steroidal anti-inflammatory agent, Ketoprofen to give a final concentration of 5% (w/w). The resulting admixture contains 500 mg Ketoprofen in 9.50 grams Kenalog. Topical application of the mixture is made directly to the area of maxillary alveolar tenderness in 60 mg (0.06 ml) to 250 mg (0.250 ml) amounts using a small syringe.

EXAMPLE 3

A cream formulation of a nonsteroidal anti-inflammatory agent Ketoprofen is prepared by thoroughly mixing the Ketoprofen (w/w) in a sterile cream base (Schering® base); two grams of Ketoprofen in 8 grams of cream. Amounts of the mixture of from 0.06 ml to 0.25 ml are applied to the central portion of the pressure sensitive adhesive surface of an oral adhesive bandage. The drug containing bandage is then applied directly on the area of tenderness.

What is claimed is:

1. Composition for reducing or eliminating intraoral inflammation localized in the maxillary third molar apical area associated with migraine, tension headaches, post traumatic headache, facial pain and cervical muscle spasm which consists essentially of at least one NSAID selected from the group consisting of aspirin, ibuprofen, naproxen, and ketoprofen and a glucocorticoid steroid in a pharmacologically acceptable carrier adapted for delivering and enabling temporary adherence of the composition to the mucous membrane of the mouth in the maxillary third molar apical area.

2. Method of reducing or eliminating intraoral inflammation localized in the maxillary third molar apical area associated with migraine, tension headaches, post-traumatic headache, facial pain and cervical muscle spasm which comprises topically applying directly to the mucous membrane of the mouth in the maxillary, third molar apical area a composition consisting essentially of at least one non-steroid anti-inflammatory medication selected from the group consisting of aspirin, ibuprofen, naproxen, and ketoprofen in addition to a glucocorticoid steroid in a pharmaceutically effective form and amount for delivering and enabling temporary adherence of the composition to the mucous membrane of the mouth in the maxillary third molar apical area.

3. Method according to claim 2 wherein said pharmaceutically effective form is selected from the group consisting of ointments, creams, lotions, gels, powders, tablets, pastes, films, tapes and adhesive bandages.

4. Method according to claim 2 wherein said non-steroid medication is used in combination with a glucocorticoid steroid.

* * * * *